US00PP15819P2

(12) United States Plant Patent
Olesen et al.

(10) Patent No.: US PP15,819 P2
(45) Date of Patent: Jun. 28, 2005

(54) ROSE PLANT NAMED 'POULCS010'

(50) Latin Name: *Rosa hybrida*
Varietal Denomination: POULcs010

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 19 days.

(21) Appl. No.: 10/812,701

(22) Filed: Mar. 29, 2004

(51) Int. Cl.[7] ..... A01H 5/00
(52) U.S. Cl. ..... Plt./150
(58) Field of Search ..... Plt./150, 146

*Primary Examiner*—Anne Marie Grunberg
*Assistant Examiner*—June Hwu

(57) ABSTRACT

A new garden rose plant of the compact floribunda class which has abundant, orange red flowers and attractive foliage. This new and distinct variety has shown to be uniform and stable in the resulting generations from asexual propagation.

2 Drawing Sheets

Botanical classification: *Rosa hybrida.*
Variety denomination: 'POULcs010'.

SUMMARY OF THE INVENTION

The present invention constitutes a new and distinct variety of garden rose plant which originated from a controlled crossing between the female seed parent, an unnamed seedling, and the male parent named 'Deltogo', nonpatented. The two parents were crossed during the summer of 1992 and the resulting seeds were planted in a controlled environment in Fredensborg, Denmark. The new variety is named 'POULcs010'.

The new variety may be distinguished from its unnamed seed parent by the following combination of characteristics:

1. The seed parent has salmon pink flowers while 'POULcs010' has a orange red flower color.
2. The seed parent is a more upright in growth habit while 'POULcs010' is low growing, compact floribunda.

The new variety may be distinguished from its pollen parent, 'Deltogo' by the following combination of characterictics:

1. The pollen parent has an apricot blend flower color while flowers of 'POULcs010' are orange red.
2. 'POULcs010' is more compact than the pollen parent.

The objective of the hybridization of this rose variety was to create a new and distinct variety for garden use with unique qualities, such as:

1. Uniform and abundant orange red flowers;
2. Vigorous, but compact growth when propagated both as a budded rose and on its own roots;
3. Disease resistance;
4. Attractive, dark colored foliage.

This combination of qualities is not present in previously available commercial cultivars of this type, known to the inventors, and distinguish 'POULcs010' from all other varieties of which we are aware.

As part of their rose development program, L. Pernille Olesen and Mogens N. Olesen germinated the seeds from the aforementioned hybridization during winter 1992–1993 and conducted evaluations on the resulting seedlings in a controlled environment in Fredensborg, Denmark.

'POULcs010' was selected in the spring 1993 by the inventors as a single plant from the progeny of the aforementioned hybridization.

Asexual reproduction of 'POULcs010' by traditional budding and rooted cuttings was first done by L. Pernille and Mogens N. Olesen in their nursery in Fredensborg, Denmark in June 1993. This initial and other subsequent asexual propagations conducted in controlled environments have demonstrated that the characteristics of 'POULcs010' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULcs010'. Specifically illustrated in Sheet 1:

FIG. 1.1; Open flower, stem showing cluster of open flowers, branching, and the attachment of and peduncles;

FIG. 1.2; Flower bud closed, flower bud as sepals unfold, and partially open;

FIG. 1.3; Flower petals, detached;

Specifically illustrated in Sheet 2:

FIG. 2.1; Sepals, receptacle, and peduncle;

FIG. 2.2; Juvenile leaves;

FIG. 2.3; Mature leaf;

FIG. 2.4; Bare stems exhibiting thorns.

DETAILED DESCRIPTION OF THE VARIETY

The following is a description of 'POULcs010', as observed in its growth in a field nursery in Jackson County, Oreg. Observed plants are 2 years of age and were budded on to *Rosa multiflora* rootstock. Color references are made using The Royal Horticultural Society (London, England) Colour Chart, 1995, except where common terms of color are used.

For a comparison, several physical characteristics of the rose variety 'POULac006', a rose variety from the same inventors described and illustrated in U.S. Plant Patent application Ser. No. 10/342,702 (now abandoned) are compared to 'POULcs010' in Chart 1.

CHART 1

| | 'POULcs010' | 'POULac006' |
|---|---|---|
| General Tonality | Red Group 43A to 43B. | Red Group 40A. |
| Petal Count | 30 to 35. | 35 to 40. |
| Bloom Diameter | 50 to 55 mm. | 60 mm. |

FLOWER AND FLOWER BUD

Blooming habit: Continuous.

Flower bud:

*Size.*—Upon opening, 25 mm in length from base of receptacle to end of bud. Diameter is 10 mm on average.

*Bud form.*—Pointed ovoid.

*Bud color.*—As sepals unfold, petals are Red Group 41A with intonations of Red Group 46B.

*Sepals.*—

*Upper surface.*—Color: Green Group 138B to 138A. Surface: Moderately pubescent.

*Lower surface.*—Color: Yellow-Green Group 144A. Anthocyanin: Greyed-Purple Group 183B. Shape: Sepal apex is cirrhose. Base is flat at union with receptacle. Margins have strong to medium foliaceous appendages on three of the five sepals. Size: 22 mm (l)×7 mm (w).

*Receptacle.*—Surface texture: Smooth and lightly glaucous. Shape: Pear to urn-shaped. Size: 8 mm (h)×5 to 6 mm (w). Color: Yellow-Green Group 144A. Anthocyanic pigments the color of Greyed-Purple Group 183A observed.

*Pedicel.*—Surface: Smooth. Stipitate glands are sparse. Length: 35 to 40 mm average. Diameter: 2.5 mm. Color: Yellow-Green Group 144B. Anthocyanic pigments the color of Greyed-Purple Group 183A observed. Strength: Somewhat strong.

*Borne.*—Multiples of 5 buds per flowering stem.

Flower bloom:

*Fragrance.*—Light rose scent.

*Duration.*—The blooms have a duration on the plant of approximately 7 to 10 days. After flowers have fully matured, petals fall cleanly away from plant.

*Size.*—Average flower diameter is 50 to 55 mm when open. Average flower depth is 23 mm.

*Form.*—General shape is a shallow cup fully opening to expose reproductive stamens and stigmas.

*Shape of flower when viewed from the side.*—Upon opening, upper part: Flat. Upon opening, lower part: Flat. Open flower, upper part: Flattened Convex. Open flower, lower part: Concave.

Petalage: Average range is 30 to 35 petals under normal conditions with 6 petaloids.

Color:

Upon opening, petals:

*Outermost petals.*—Outer side: Red Group 43C. Inner side: Red Group 40A.

*Innermost petals.*—Outer side: Red Group 43C. Inner side: Red Group 40A.

Upon opening, basal petal spots:

*Outermost petals.*—Outer side: Yellow Group 4B. Inner side: Yellow Group 4A.

*Innermost petals.*—Outer side: Yellow Group 4B. Inner side: Yellow Group 4A.

After opening, petals:

*Outermost petals.*—Outer side: Red Group 43C. Inner side: Red Group 40A.

*Innermost petals.*—Outer side: Red Group 43C. Inner side: Red Group 40A.

After opening, basal petal spots:

*Outermost petals.*—Outer side: Yellow Group 4B. Inner side: Yellow Group 4A.

*Innermost petals.*—Outer side: Yellow Group 4B. Inner side: Yellow Group 4A.

General tonality: On open flower Red Group 43A to 43B. Color does not change as the flower matures.

Petals:

*Petal reflex.*—None.

*Margin.*—Entire and somewhat undulate.

*Shape.*—Apex: Round with occasional cleft. Base: Acute.

*Size.*—30 mm (l)×30 mm (w).

*Thickness.*—Thin.

*Arrangement.*—Not Formal.

Petaloids:

*Quantity.*—5 to 8 in number.

*Color.*—Upper surface: Red Group 40A. Lower surface: Red Group 43C.

*Size.*—25 mm (l)×12 mm (w).

Reproductive organs:

*Pistils.*—Length: 4 mm long. Quantity: 32 actual count.

*Pollen.*—None observed.

*Anthers.*—Size: 2 mm long. Color: Greyed-Orange Group 167A. Quantity: 65 actual count.

*Filaments.*—Color: Yellow Group 9A to 9C. Length: 6 to 7 mm.

*Stigmas.*—Inferior relative to the filament length and height of the anthers. Color: Greyed-Yellow Group 160C.

*Styles.*—Length: 7 mm. Color: White Group 155A. Other intonations: None.

*Hips.*—None Observed in the field nursery in Jackson County Oreg.

PLANT

Plant growth: Moderate, upright to bushy. When grown as a budded field grown plant on *Rosa multiflora* understock, the average height of the plant is 60 to 100 cm and the average width is 100 cm.

Stems:

*Color.*—Young wood: Yellow-Green Group 144A. Older wood: Yellow-Green Group 144C.

*Surface texture.*—Young wood: Smooth. Older wood: Smooth.

*Thorns.*—Incidence: 14 thorns per 10 cm of stem. Size: Average length: 5 mm. Juvenile color: Greyed-Purple Group 184A. Mature color: Greyed-Orange Group 176A. Shape: Concave.

Plant foliage: Normal number of leaflets on normal leaves in middle of the stem: 7 leaflets.

*Compound leaf size.*—80 mm in length by 50 mm wide.

*Quantity.*—Average.

*Color.*—Mature foliage: Upper leaf surface: Green Group 137A to Yellow-Green Group 146A. Lower leaf surface: Yellow-Green Group 146B. Juvenile foliage: Upper leaf surface: Greyed-Purple Group 183A. Lower leaf surface: Greyed-Purple Group 185A. Anthocyanin: Location: Upper and lower surfaces of juvenile leaflets.

Plant leaves and leaflets:

*Stipules.*—Size: 20 mm in length. Quantity: 2 per compound leaf. Shape: Linear with outward extending apecies. Color: Yellow-Green Group 144B. Margins: Few stipitate glands. Anthocyanin: None.

*Petiole.*—Length: 30 mm. Diameter: 2 mm. Color: Yellow-Green Group 144B. Underneath: Thorns. Anthocyanin: Light intonations of Greyed-Red Group 181C observed on upper surface.

*Rachis.*—Length: 35 mm. Color: Yellow-Green Group 144B. Underneath: Thorns. Anthocyanin: Light intonations of Greyed-Red Group 181C observed on upper surface.

*Leaflet.*—Leaflet size: 28 mm in length by 20 mm wide. Edge: Serrated. Shape: Generally ovate. Leaflet apecies are cuspidate. Base is rounded. Texture: Thick. Arrangement: Odd pinnate. Venation: Reticulate. Glossiness: Glossy.

Disease resistance: Above average resistance to mildew, rust, black spot, and *Botrytis* under normal growing conditions in Jackson County, Oreg.

Cold hardiness: The variety 'POULcs010' has been found to be cold tolerant to USDA Cold Hardiness Zone 6.

It is claimed:

1. A new and distinct variety of rose plant of the floribunda rose class, substantially as herein illustrated and described as a distinct and novel rose variety due to its abundant orange red flowers, disease resistance, and extended period of bloom.

* * * * *

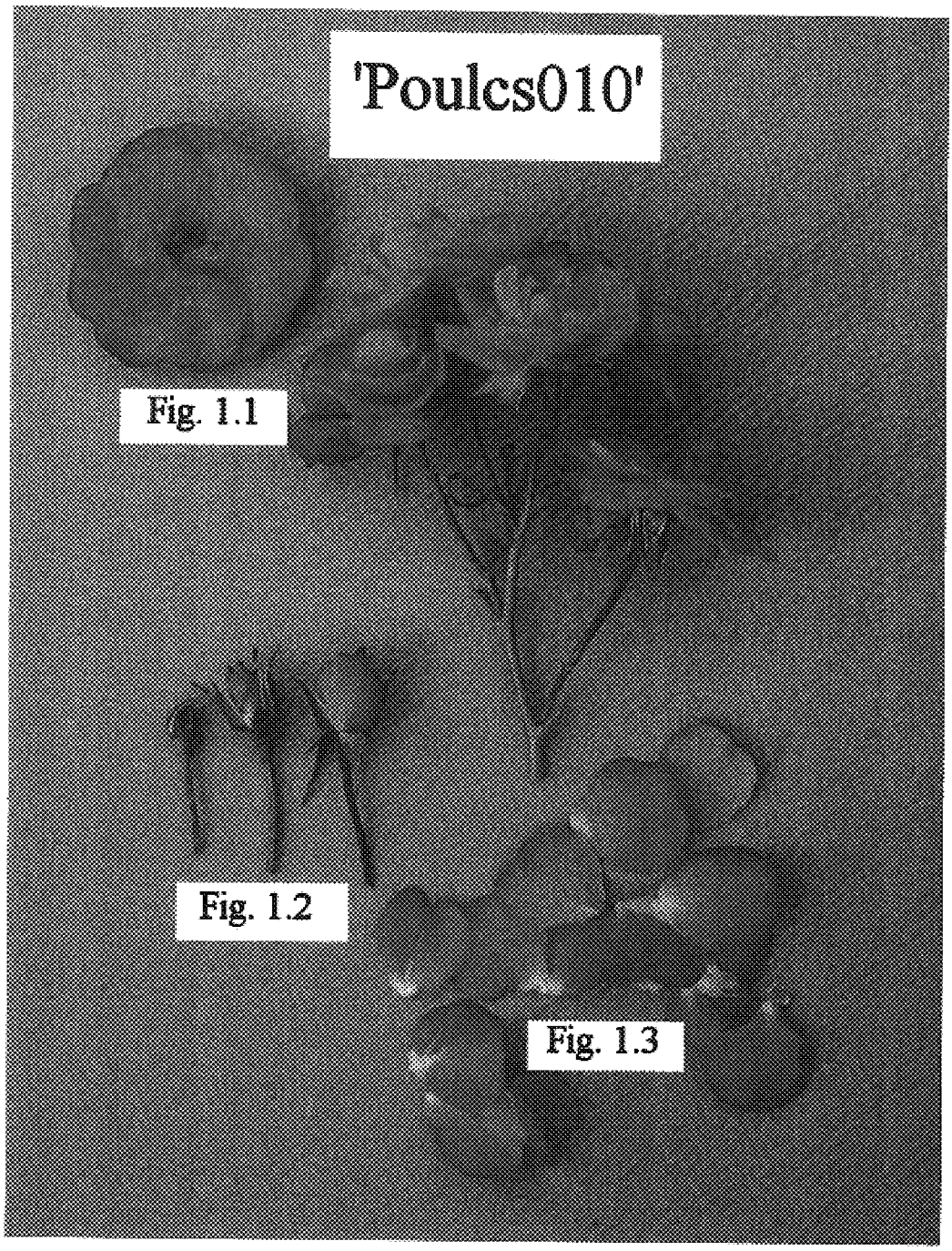
'Poulcs010'
Fig. 1.1
Fig. 1.2
Fig. 1.3

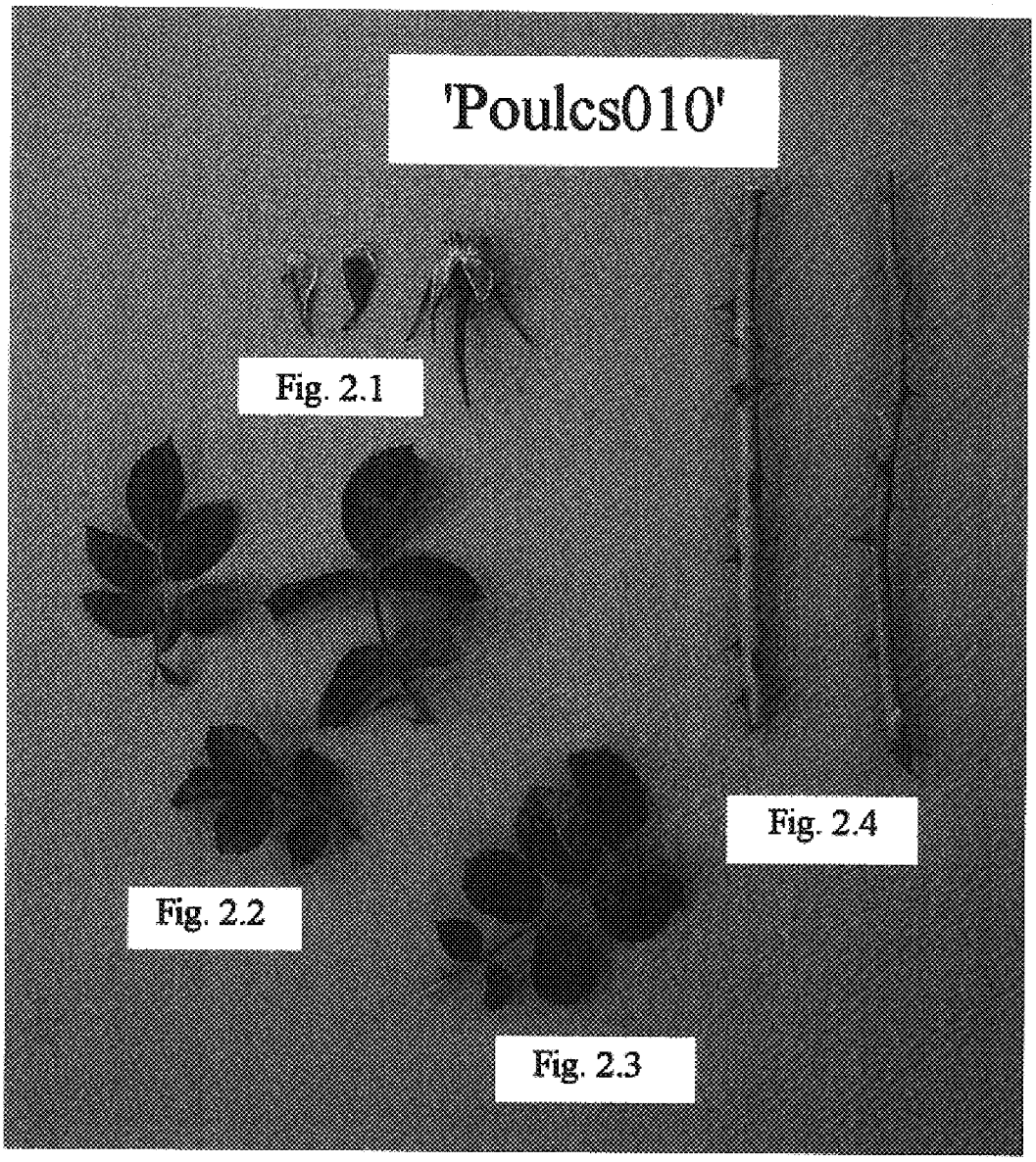
'Poulcs010'
Fig. 2.1
Fig. 2.2
Fig. 2.3
Fig. 2.4